United States Patent [19]

Kashiwayama

[11] Patent Number: 4,554,161

[45] Date of Patent: Nov. 19, 1985

[54] DERMATIC MEDICAMENT

[76] Inventor: Shinei Kashiwayama, No. 558 Iwasak, Kamitonda-machi, Nishimuro-gun, Japan

[21] Appl. No.: 578,308

[22] Filed: Feb. 9, 1984

Related U.S. Application Data

[62] Division of Ser. No. 261,167, Apr. 27, 1981, Pat. No. 4,503,041.

[30] Foreign Application Priority Data

Sep. 1, 1979 [JP] Japan .................................. 54-112294

[51] Int. Cl.⁴ ............................................. A61K 35/72
[52] U.S. Cl. .................................................... 424/115
[58] Field of Search ......................................... 424/115

[56] References Cited

PUBLICATIONS

American Type Culture Collection Catalog of Strains, 15th Edition, 1982, pp. 357, 377, 376, 526 and 527.

Primary Examiner—Lionel M. Shapiro
Attorney, Agent, or Firm—Bucknam and Archer

[57] ABSTRACT

A novel strain Trichosporon Kashiwayama, a culture product or culture liquid of said strain, sterile liquid, sterile filtrate, sterile supernatant of said culture liquid, or concentrate or dry product thereof, processes for preparations thereof, a dermatic medicament having curative effect of skin disorder or a cosmetic consisting solely of or comprising as a main ingredient the above product, liquid, filtrate, supernatant, concentrate or dry product.

2 Claims, No Drawings

DERMATIC MEDICAMENT

This application is a division, of application Ser. No. 261,167, filed Apr. 27, 1981, now U.S. Pat. No. 4,503,041, issued Mar. 5, 1985.

TECHNOLOGICAL FIELD

The present invention relates to a dermatic medicament consisting solely of a sterile supernatant formed by filtering and sterilizing a culture liquid of a novel strain, Trichosporon Kashiwayama strain (deposited at FRI with deposition No. 4821) (FERM-P No. 4821), which may be identified as a strain belonging to the genus Geotricum or Endomycopsis, according to customary procedures, or a concentrate or dry product formed from said sterile supernatant according to customary procedures, or a dermatic medicament comprising as the active ingredient said sterile supernatant or said concentrate or dry product incorporated into a carrier such as an ordinary skin cream or ointment base.

BACKGROUND OF THE INVENTION

The microorganism that is used in the present invention, that is, Trichosporon Kashiwayama strain, is considered to belong to yeast, but the strain sometimes is classified as a fungi imperfecti. Accordingly, the statement that the strain may be identified as a strain belonging to the genus Geotricum or Endomycopsis is based on the scientific concept held by experts in the art.

The strain that is used in the present invention is characterized in that it has bead-like arthrospores and pseudomycelia. Moreover, the strain is characterized in that a fermentation product of the strain, that is, a supernatant of a culture liquid of the strain, has by itself a prominent medicinal effect to the human skin.

Description of the Invention

The effective substance which exerts a medicinal effect is still unknown. However, if a sterile supernatant of a culture liquid of the strain or a concentrate or dry product is applied to the skin as it is or after it has been mixed with an appropriate carrier and formed into a preparation suitable for application to the human skin, for example, an ointment, the following medicinal effects can be attained.

(1) The fermentation liquid is weakly acidic (having a pH value of 4.5 to 5.0) and is non-toxic to the skin, and it promotes the skin-protecting action of the fat membrane, especially the bacterium controlling action inherent of the fat membrane.

(2) Excessive peeling of ceratine pieces from the horny layer is prevented and simultaneously, an appropriate water content is maintained in the horny layer, and therefore, the characteristics of the skin per se such as dampness and elasticity can be maintained in good conditions.

(3) The lipid metabolism of epidermal cells is controlled to promote appropriate formation of keratin and smooth propagation and differentiation of epidermal cells.

(4) Especially to the fatty skin, excessive secretion of sebum is controlled and increase of the thickness of the fat membrane is prevented. Accordingly, diffusion of sebum to the skin surface from the hair follicle is promoted and a preventive effect to fatty dermatitis such as acne is obtained.

(5) Since collagen fibers of the statum reticulate are reinforced or swollen to maintain an appropriate water content in the upper layers, good and normal hardness and elasticity are held in the skin.

(6) Since circulation of blood is improved, metabolism of the skin is promoted, and transportation of skin waste matters to the vein and excretion thereof are promoted. Simultaneously, excretion of melanin color to the outside of the body is expedited.

(7) To the skin diseases caused by oxidation under actinic rays, the fermentation liquid or sterile supernatant thereof acts as the antioxidant to the fatty membrane and promotes discoloration of abnormally deposited melanin color in skin spots or the like. When the fermentation liquid or sterile supernatant thereof is administered in combination with the infrared ray irradiation treatment or oral administration of vitamin E, there can be attained a preventive or curative synergistic effect to contact dermatitis, skin spots and abnormal color deposition owing to the heliosensitivity.

The micological properties of the Trichosporon Kashiwayama strain (deposited at FRI with deposition No. 4821) that is used in the present invention will now be described.

(1) Morphological Properties:

1. Shape and Size (malt extract-MY liquid medium):

After 3 days' culturing at 25° C., there are obsrved cells having a rectangular or oval shape and a size of (3 to 4$\mu$)×(3 to 20$\mu$), and when culturing is conducted for 5 days or more, the shape of cells becomes irregular and finally, cells become mycelioid.

2. Formation of Pseudomycelia (slide culture on potato extract agar culture medium):

Cells are pseudohyphal or pseudomycelial, and they have characteristic zigzag arthrospores but no conidia.

3. Ascospores:

Cells have no ascospores.

4. Ballistospores:

Cells have no ballistospores.

(2) Characteristic Properties on Culture Media:

1. Colony on Agar Streak Culture Medium (malt extract-MY agar culture medium):

Dull, white, hairy and rough surface, very soft, not raised but flat, ciliate periphery.

2. Film on Liquid Culture Medium (malt extract-MY liquid culture medium):

White, hairy, flocculent and tough film is formed.

(3) Physiological Properties:

1. Saccharide Fermentation:

Non-fermentative to glucose, galactose, sucrose, lactose, treharose, raffinose and inullin.

2. Saccharide Utilization (Assimilation):

D-glucose+, D-galactose+, maltose—, raffinose—, sucrose—, lactose—, sodium lactate+, D-xylose+, erythritol—, D-mannitol+, L-sorbose+, inositol—, treharose—, D-arabinose—, L-arabinose—, sodium succinate+, sodium citrate+, sodium acetate+, inullin—, soluble starch—, ethanol+, glycerol+, cellobiose—.

Note

+: utilized

—: not utilized

3. Utilization of Nitrates:

Not utilized.

4. Utilization of Nitrites:

Not utilized.

5. Utilization of Ethylamine Hydrochloride:

Not utilized.

6. Decomposition of Glucoside (Arbutin):

Decomposed.
7. Formation of Starch Analogues:
Not formed.
8. Formation of Pigment:
Not formed.
9. Formation of Esters:
Formed.
10 Litmus Milk Reaction:
Not coagulated.
11. Vitamin Demand:
Not required.
12. Salt Resistance:
Critical concentration of 6 to 8 w/v %.
13. Optimum Temperature:
25° C.
14. Optimum pH Value:
5.0.
15. Decomposition of Urea:
Not decomposed.
16 Growth on 50% (w/w) Glucose Agar or 60% (w/w) Yeast Extract Agar Medium:
Not growth.
17. Growth at 37° C.:
No growth.
18. Formation of Acid from Glucose:
Not formed.
19. Resistance to Cycloheximide:
Resistant.
20. Decomposition of Oil and Fat:
Decomposed.
4. Other Mycological Characteristics:
1. Production of Fragrance:

The present strain is characterized by production of a fragrance component. From the results of gas chromatography, it was found that the fragrance component is composed mainly of ethanol, ethyl acetate, isopropyl alcohol, isopropyl acetate, isobutyl alcohol, isobutyl acetate, isoamyl alcohol and isoamyl acetate. The fragrance is a so-called apple fragrance. The present strain is characteristic over known yeasts having a fragrance-producing property in that formation ratios of not only higher alcohols but also esters thereof are high.

Optimum conditions for production of these neutral fragrance ingredients are as follows.

(a) Initial pH value of 4.0 to 5.0 and maintenance of low pH value during fermentation.

(b) Total nitrogen content of 400 to 500 mg/liter culture medium.

As the inorganic nitrogen source, there are preferably used ammonium sulfate, ammonium nitrate and ammonium chloride, and as the organic nitrogen source, there are preferably used yeast extract, casamino acid and peptone. Furthermore, good results are obtained when amino acids such as leucine, isoleucine, valine and phenylalanine are added.

(c) Selection of carbon sources.

Glucose, galactose, ethanol and glycerol are suitable. A preferred saccharide concentration is 5%.

(d) Cell inoculation ratio of 1 to 2%.

(4) Culturing temperature of 25° to 30° C.
Stationary culture is preferred.

2. Formation of Organic Acids:

Formic acid, propionic acid, n-butyric acid, succinic acid and citric acid are formed from glucose.

Customary yeast culture media may be used for the production of a dermatic medicament by using the Trichosporon Kashiwayama strain according to the present invention. According to one preferred embodiment, shaking or stationary culture is carried out at 20° to 30° C. for about 24 hours in a solid or liquid medium comprising 0.3% (w/v) of glucose, 0.5% (w/v) of skim milk and 0.05% (w/v) of yeast extract and having a pH value of 4.0 to 6.0, and the same culture medium as mentioned above is inoculated with the resulting culture product as the seed and stationary culture or shaking culture is carried out at 20° to 30° C. for 3 to 7 days.

The culture liquid is subjected to filtration and removal of cells according to customary procedures, for example, by using a membrane filter, and the cell-free supernatant is concentrated, for example, under reduced pressure, preferably at a concentration rate of 4 to 25. The resulting concentrate is sterilized according to customary procedures and stored at room temperature or in a refrigerator.

An example of the cell-free supernatant prepared according to the present invention have properties shown in Table 1.

TABLE 1

A cell-free purified filtrate of the supernatant of the culture product of the present strain comprises small amounts of amino acids, saccharides and lipids. When the filtrate is quantitatively determined, it is seen that the total nitrogen content is 0.005 to 0.015% and the total phosphorous content is 0.004 to 0.014%.

1. Nature and State:

The filtrate is a colorless-to-slightly yellowish transparent liquid and has a faint fragrance.

2. Confirmation Tests:

(1) 20 ml of the filtrate is evaporated on a water bath until the volume is reduced to about 50 ml. Then 1 ml of ninhydrin test solution is added to the concentrate. When the mixture is heated for 30 minutes, the liquid comes to have a violet color. (2) 5 ml of nitric acid is added to the concentrate formed by conducting evaporation in the same manner as described in (1) above, and the mixture is boiled for 20 minutes. After the mixture is cooled, it is neutralized with a 10% solution of sodium hydroxide. Then, 2 ml of ammonium molybdate test solution is added to the mixture. If the mixture is heated, the liquid becomes yellowish. If a 10% solution of sodium hydroxide is added to the liquid, it becomes colorless.

(3) 10 mg of indole and 2 ml of hydrochloric acid are added to 5 ml of the filtrate, and the mixture is shaken sufficiently. When the mixture is then heated for 10 minutes, the liquid becomes red.

3. Physical Properties:

(1) Specific gravity ($d_{25}^{25}$): 1.000 to 1.015.
(2) Refractive index ($n_D^{25}$): 1.330 to 1.340.
(3) pH (25° C.): 4.5 to 5.5.

4. Evaporation Residue:

0.5 to 2.0%.

Analysis value of an example of the concentrate (concentration rate of 2) of the cell-free supernatant prepared according to the present invention are shown in Table 2.

TABLE 2

| | |
|---|---|
| Water content (according to the atmospheric pressure drying method): | 98.7% |
| Protein (coefficient of 6.25): | trace |
| Lipid content (according to Soxhlet extraction method): | 0.2% |
| Fiber content: | 0% |

TABLE 2-continued

| | |
|---|---|
| Ash content: | 0.1% |
| Sugar content: | 1.0% |
| Total solid content*: | 1.3% |
| Amino form nitrogen content: | 10 mg % |
| Titration acidity: | 0.6** |
| Volatile base form nitrogen content: | 1 mg % |
| Arsenic content (as $As_2O_3$): | not detected (detection limit: 0.1 ppm) |
| Heavy metal content (as Pb): | not detected (detection limit: 1 ppm) |
| Total mercury content: | not detected (detection limit: 0.01 ppm) |
| Cadmium content: | not detected (detection limit: 0.01 ppm) |
| Calcium content: | 14.7 mg % |
| Phosphorus content: | 9.8 mg % |
| Formic acid content: | not detected (detection limit: 0.1%) |
| Acetic acid content: | not detected (detection limit: 0.01%) |
| Butyric acid content: | not detected (detection limit: 0.01%) |
| Lactic acid content: | 0.06% |
| Citric acid content: | 0.02% |
| Living cell number: | less than 30 cells per ml. |
| E. coli: | (−) |
| Staphylococcus aures: | (−) |
| Number of fungi: | (−)/ml |
| Number of yeasts: | (−)/ml |
| Propionic acid content: | not detected (detection limit: 0.02 g/Kg) |
| Sorbic acid content: | not detected (detection limit: 0.005 g/Kg) |
| Benzoic acid: | 0.42 g/Kg |
| p-Hydroxybenzoic acid ester: | not detected (detection limit: 0.005 g/Kg) |
| Vitamin $B_1$ content: | not detected (detection limit: 0.01 mg %) |
| Vitamin $B_2$ content: | 0.02 mg % |
| Total vitamin C content: | not detected (detection limit: 2 mg %) |
| Vitamin $B_6$ content: | not detected (detection limit: 5 μg %) |
| Vitamin $B_{12}$ content: | not detected (detection limit: 0.05 μg %) |
| Pantothenic acid content: | 0.09 mg % |
| Choline content: | not detected (detection limit: 0.03%) |
| Folic acid content: | not detected (detection limit: 1 μg %) |
| Niacin content: | not detected (detection limit: 0.03 mg %) |
| Total carotene content: | not detected (detection limit: 0.02 mg %) |
| pH value: | 4.9 |
| Amino acid composition***: | |
| Arginine: | below 0.01 |
| Lysine: | below 0.01 |
| Histidine: | below 0.01 |
| Phenylalanine: | below 0.01 |
| Tyrosine: | below 0.01 |
| Leucine: | below 0.01 |
| Isoleucine: | below 0.01 |
| Methionine: | below 0.01 |
| Valine: | below 0.01 |
| Alanine: | below 0.01 |
| Glycine: | below 0.01 |
| Proline: | below 0.01 |
| Glutamic acid: | 0.01 |
| Serine: | below 0.01 |
| Threonine: | below 0.01 |
| Aspartic acid: | below 0.01 |
| Tryptophane: | below 0.01 |
| Cystine: | below 0.01 |

Note
*% based on water
**number of ml of 1N alkali titrated for neutralizing 100 g of sample
***g of amino acid in 100 g of sample (cystine: performic acid oxidation method, tryptophane: microogranism assay)

Of course, the cell-free sterile supernatant can be used as a dermatic medicament without concentration. However, from the viewpoint of the storage or the like, it is preferred that the cell-free sterile supernatant be concentrated. Furthermore, a high concentrate of a concentration rate of more than 25 to a dry product may be used. Such concentrate, high concentrate or dry product may be used as a dermatic medicament as it is. Furthermore, a dermatic medicament of the present invention can be formed by mixing such concentrate, high concentrate or dry product with a cream, an ointment base or other carrier.

When a concentrate formed by concentrating the above cell-free sterile supernatant at a concentration rate of 4 is analyzed, it is seen that various amino acids and vitamins are contained. However, since the analysis is made for generic terms, it will readily be understood that even if the respective components are mixed according to the found analysis values, a dermatic medicament of the present invention cannot be prepared. In other words, it is believed that the activities of the dermatic medicament of the present invention are due to unknown components outside the analysis items.

Results of the toxicity test using chicken embryo prove that the above-mentioned cell-free sterile concentrate (concentration rate of 4) has no toxicity. Furthermore, results of the human body patch test and continuous human skin irritation test prove that the concentrate is not toxic to the human skin at all. Moreover, results of the rabbit eye irritation test prove that the concentrate is not irritative at all. Still further, results of the antibiotic test prove that the concentrate contains no antibiotic substance.

It has been confirmed that the dermatic medicine of the present invention has curative effects to skin spots, chapped skin, contact dermatitis and burnt skin. These curative effects will now be described with reference to the following Experiments.

HUMAN BODY PATCH TEST

Fifty women (suffering from some skin disease or other and going to dematological hospitals), who were 23 to 44 years old, were chosen for the test. Adhesive plasters having a size of 4 cm×4 cm and containing about 0.2 g of the concentrate (concentration rate of 2) of the present invention were applied to the inner side of the left upper arm and the paravertebral region of the back, and after 48 hours, the plasters were removed and the applied regions were examined. In each of the patients, the inner side of the left upper arm or the paravertebral region was not adversely affected.

CONTINUOUS HUMAN SKIN IRRITATING TEST

Sterilized gauze pieces having an area of 10 $cm^2$ were impregnated with about 5 ml of the concentrate (concentration rate of 2) of the present invention, and they were applied to the right check regions of 45 women 23 to 45 years old (35 women suffered from some skin disease or other and received the medical treatment at a dematological hospital and remaining 10 women were employees of this hospital) for 15 minutes. This treatment was conducted for 40 days continuously. No reaction was observed in any of these women, and troubles such as erythema were not caused at all.

RABBIT EYE IRRITATING TEST

Three white rabbits were used as test animals. In advance, it was confirmed that their eyes had no abnormal signs. In each rabbit, 0.1 ml of the concentrate (concentration rate of 2) of the present invention was dropped to the right eye and 0.1 ml of a blank liquid was dropped to the left eye. Just after dropping and 3, 6, 24, 48 and 72 hours after dropping, both the eyes were checked by using a slit lamp. Abnormal signs such as congestion of the cornea, iris or conjuctiva were not observed at all.

SKIN SPOT REMEDY TEST

621 Women having skin spots on the face, exclusive of patients of liver diseases or female disorders and pregnant women, who were going to dematological hospitals for remedy of skin spots, were selected. After washing of the face, the skin pores were opened by ozone and steam, and gauze impregnated with the concentrate (concentration rate of 2) of the cell-free supernatant of the present invention was applied to the spot-occurring region. The applied gauze was covered with a tape of Saran-Wrap and infrared ray irradiation was carried out for 15 to 20 minutes to cause the concentrate to permeate into the skin. This treatment was conducted once a week and continued for 3 months. It was found that the condition was highly improved in 363 women (58.4%), the condition was relatively improved in 122 women (19.8%), no improvement was observed in 133 women (21.4% ), the condition was worsened in one woman (0.01%) and contact dermatitis was observed in the remaining 2 women (0.03%) (it is considered that contact dermatitis was caused for the reason irrelevant to this treatment). The ratio of the patients in which the condition was highly or relatively improved was as high as 80%. Furthermore, in 60% of 365 women in which the condition was highly improved, the skin spots disappeared completely.

TEST OF REMEDY OF SKIN CHAPPING AND FINE WRINKLES

Ordinarily, women more than 25 to 30 years old are nervous about the skin chapping and fine wrinkles and especially in women 35 to 40 years old, this tendency is conspicuous, though women more than 40 years old are similarly nervous about the skin chapping and fine wrinkles. In this test, 962 women who are going to dematological hospitals were selected (150 women 25 to 30 years old, 218 women 30 to 35 years old, 248 women 35 to 40 years old, 172 women 40 to 50 years old and 174 women more than 45 years old). After washing of the face skin, skin holes were opened by ozone and steam and gauze impregnated with the concentrate (concentration rate of 2) of the cell-free supernatant of the present invention was applied closely to the face skin and the gauze was covered with a tape of Saran-Wrap. Infrared ray irradiation was conducted for 15 to 20 minutes to cause the concentrate to permeate into the skin. It was found that after one treatment, the chapped skin was highly improved in 698 women (73%), the chapped skin was relatively improved in 156 women (16%), the condition was not changed in 72 women (7%) and the condition was not worsened in any of the women tested, with the rest being 36 women (4%). In view of the fact that the chapped skin is advanced to fine wrinkles, it is considered that the concentrate of the present invention, which is effective for remedy of the chapped skin, has a preventive effect to formation of fine wrinkles.

TEST OF CURATIVE EFFECT TO CONTACT DERMATITIS

A woman 21 years old, who had suffered from rash and itch on the lids of both the eyes from the next day after exchange of an eye shadow of a company A with an eye shadow of a company B and diagnosed as contact dermatitis, was selected. Gauze impregnated with the concentrate (concentration rate of 2) of the cell-free supernatant of the present invention was applied to the affected areas by a dermatologist. Any of a steroid medicine, an anti-inflammatory agent and an anti-histaminic agent was not used at all. About 20 ml of the concentrate was given to the patient, and the concentration was coated or applied for about 30 minutes twice a day, that is, in the morning and in the evening. When 48 hours had passed from the start of the treatment, itch was removed, and after 96 hours had passed from the start of the treatment, rash substantially disappeared. After 1 week, rash was not observed at all.

TEST OF REMEDY OF BURNS AND SCALDS

A woman 47 years old having a scald by hot water on the outer portion of the left forearm (burning degree of II) with rash and swelling of a plam-like size and small blisters visited a dermatologist about 1 hour after she had get scalded. The affected area was immediately cooled with running water, and gauze impregnated with the concentrate (concentration rate of 2) of the cell-free sterile supernatant of the present invention was applied to the affected area and oilpaper was coated thereon. Then, the affected area was bandaged. When 24 hours had passed, it was found that small blisters had completely disappeared though the rash and swelling were still left, and the patient complained of no pain.

A man 30 years old, who had a scald by hot water on the back portion of the right leg (burning degree of II) with rash and swelling of a chicken egg-like size was treated with the concentrate (concentration rate of 2) of the cell-free sterile supernatant of the present invention in the same manner as described above. After 24 hours, swelling disappeared though rash was still left, and the patient complained of no pain.

Thus, it was confirmed that the concentrate of the present invention has a high curative effect to burns and scalds.

The dermatic medicament and cosmetic of the present invention will now be described with reference to the following Examples.

EXAMPLE 1

An aeration stirring fermentation tank having a capacity of 1 Kl was charged with 800 liter of a culture medium having the same composition as described hereinbefore, and after heat sterilization and natural cooling, this culture medium was inoculated with the seed formed by performing preliminary culturing at 28° C. for about 30 hours in 10 liter of the same culture medium in a small aeration stirring fermentation tank. Then, culturing was carried out at 28° C. for about 70 hours under aeration and stirring. After completion of fermentation, the culture liquid was passed through a filtering machine Model MP 293-16 manufactured by Naigai Shokuhin Kogyo Kabushiki Kaisha (filter paper GL-90 manufactured by Toyo Roshi; 0.5μ) and through a filtering machine Model MP 293-4 manufactured by the same company (membrane filter TM-2 manufactured by Toyo Roshi; 0.45μ) to remove solid particles and cells. The obtained filtrate was concentrated according to the reverse osmosis membrane method using a reverse osmosis apparatus Model R0-T10 manufactured by Bio-engineering Co. so that the volume was reduced to 200 liter. The obtained concentrate was sterilized by a plate type heat exchanger (manufactured by Iwai Kikai Kogyo Kabushiki Kaisha), sterilely packed in glass vessels and stored in a refrigerator (5° C.)

EXAMPLE 2

The sterilized concentrate obtained in Example 1 was freeze-dried, and the obtained powder was mixed with a sterile ointment base to form a dermatic ointment.

EXAMPLE 3

A cosmetic was prepared by incorporating 1 g of the sterilized concentrate obtained in Example 1 into a cosmetic base comprising 1 g of stearic acid, 7 g of bees wax, 4 g of self-emulsifiable glycerol monostearate, 30 g of liquid paraffin, 0.1 g of hydrous lanolin and 40 g of refined water and kneading the mixture according to customary procedures. The composition was poured and packed in ampoules, and the packed ampoules were marketed.

EXAMPLE 4

A medicament for the treatment of the skin was prepared by incorporating appropriate amounts of pyridoxine hydrochloride, γ-oryzanol, allantoin, DL-α-tocophenol (vitamin E) and mink oil into the composition prepared in Example 3.

POSSIBILITY OF INDUSTRIAL APPLICATION

The dermatic medicament of the present invention, which is derived from a natural source substance and is proved to be harmless, can be utilized for the treatment of dermatic disorders, for the treatment disorders of mucous membranes and for the protection of epithelia from environmental pollutions to preserve the good health as well.

We claim:

1. A dermatic medicament consisting solely of or comprising as a main ingredient a culture product or culture liquid of a novel strain, Trichosporon Kashiwayama strain (deposited at FRI with deposition No. 4821), which is a strain belonging to the genus Geotricum or Endomycopsis, a cell-removed sterile liquid, sterile filtrate or sterile supernatant of said culture product or liquid, or a concentrate or dry product thereof.

2. A cosmetic consisting solely of or comprising as a main ingredient a culture product or culture liquid of a novel strain, Trichosporon Kashiwayama strain (deposited at FRI with deposition No. 4821), which is a strain belonging to the genus Geotricum or Endomycopsis, a cell-removed sterile liquid, sterile filtrate or sterile supernatant of said culture product or liquid, or a concentrate or dry product thereof.

* * * * *